(12) United States Patent
Kristoffersen et al.

(10) Patent No.: US 11,399,844 B2
(45) Date of Patent: Aug. 2, 2022

(54) MEDICAL DEVICE HOLDING AND DELIVERY ASSEMBLY AND KIT THEREFOR

(71) Applicant: Cook Medical Technologies LLC, Bloomington, IN (US)

(72) Inventors: Jan Kristoffersen, Naestved (DK); Jens Kold, Lille Skensved (DK); Per Elgaard, Haslev (DK)

(73) Assignee: Cook Medical Technologies LLC, Bloomington, IN (US)

( * ) Notice: Subject to any disclaimer, the term of this patent is extended or adjusted under 35 U.S.C. 154(b) by 56 days.

(21) Appl. No.: 16/828,565

(22) Filed: Mar. 24, 2020

(65) Prior Publication Data
US 2020/0305882 A1 Oct. 1, 2020

(30) Foreign Application Priority Data
Mar. 26, 2019 (GB) .................................. 1904143

(51) Int. Cl.
*A61B 17/12* (2006.01)
*A61B 17/00* (2006.01)

(52) U.S. Cl.
CPC .... *A61B 17/1214* (2013.01); *A61B 17/00234* (2013.01); *A61B 17/12109* (2013.01); *A61B 2017/00238* (2013.01); *A61B 2017/1205* (2013.01)

(58) Field of Classification Search
CPC .......... A61B 17/12109; A61B 17/1214; A61B 2017/1205; A61B 17/00234; A61B 2017/00238; A61F 2/95; A61F 2/9517; A61F 2/962; A61F 2/966; A61F 2/2427; A61F 2/2436; A61F 2/011
See application file for complete search history.

(56) References Cited

U.S. PATENT DOCUMENTS 4,323,065 A * 4/1982 Kling .................... A61M 39/12
604/533
5,224,939 A * 7/1993 Holman ................ A61M 5/158
604/528

(Continued)

OTHER PUBLICATIONS

European Search Report dated Jul. 31, 2020 for EP Application No. 20275064.2.

*Primary Examiner* — Melanie R Tyson
(74) *Attorney, Agent, or Firm* — Crowell & Moring LLP

(57) ABSTRACT

A medical device holding assembly includes a carrier sheath, which carries an endoluminal medical device such as an embolization coil. The assembly also includes a housing including at least one holding element to hold the sheath, and a fixation device attached to the housing and coupled to the sheath. The fixation device includes a locking element having an unlocked configuration, which allows the sheath to slide relative to the housing, and a locked configuration, which fixes the sheath to the housing. A lock actuator is configured to lock permanently the locking element into the locked configuration. As a result, the sheath with the medical device held therewithin cannot be removed from the holding assembly during the deployment procedure, thereby ensuring that the procedure can be carried out by a single person and also protecting the integrity of the medical device before it is deployed into a patient.

19 Claims, 6 Drawing Sheets

(56) References Cited

U.S. PATENT DOCUMENTS

| | | | |
|---|---|---|---|
| 2005/0061698 A1* | 3/2005 | Delaney | A61M 25/002 206/364 |
| 2009/0204145 A1* | 8/2009 | Matthews | A61B 17/12145 606/213 |
| 2012/0330226 A1* | 12/2012 | Lee | A61B 17/12022 604/60 |
| 2014/0110296 A1* | 4/2014 | Terzibashian | A61M 25/002 206/438 |
| 2014/0276652 A1* | 9/2014 | Gittard | A61M 39/1011 604/536 |
| 2015/0119855 A1 | 4/2015 | Khalaj | |
| 2016/0082223 A1 | 3/2016 | Barnell | |
| 2018/0339128 A1* | 11/2018 | Sakaguchi | A61M 25/09 |

* cited by examiner

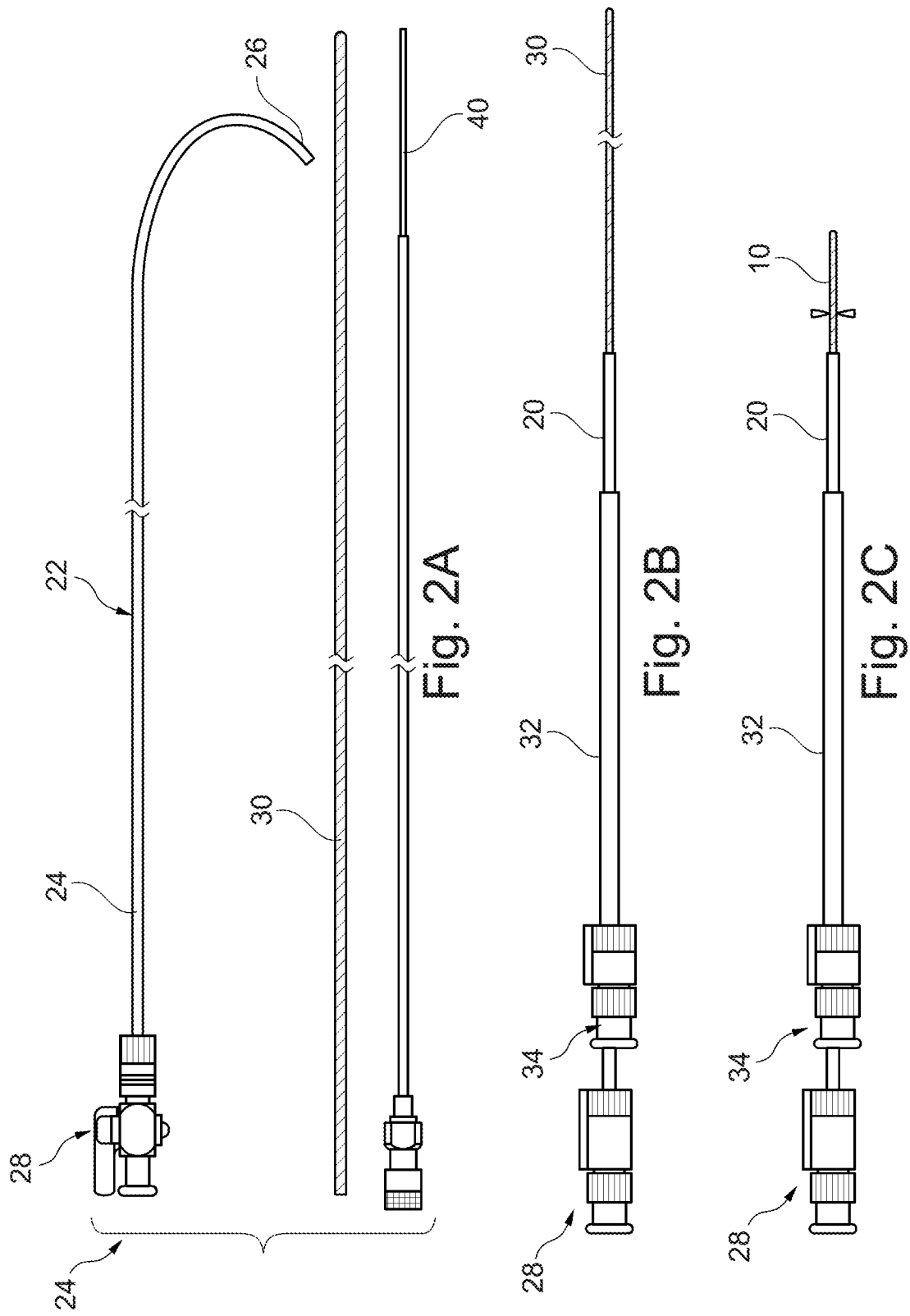

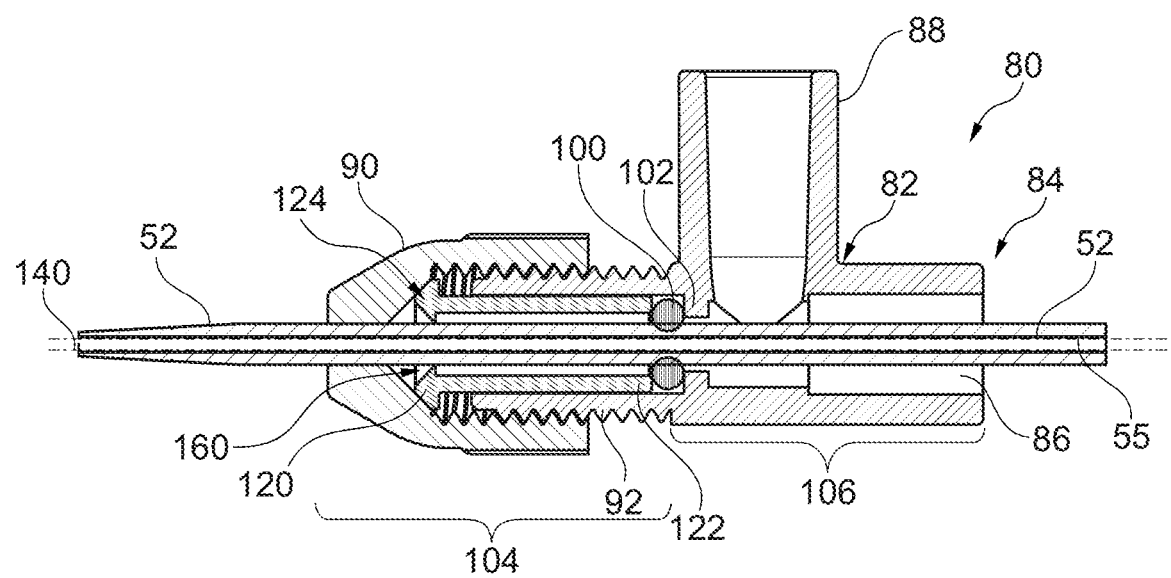
Fig. 6
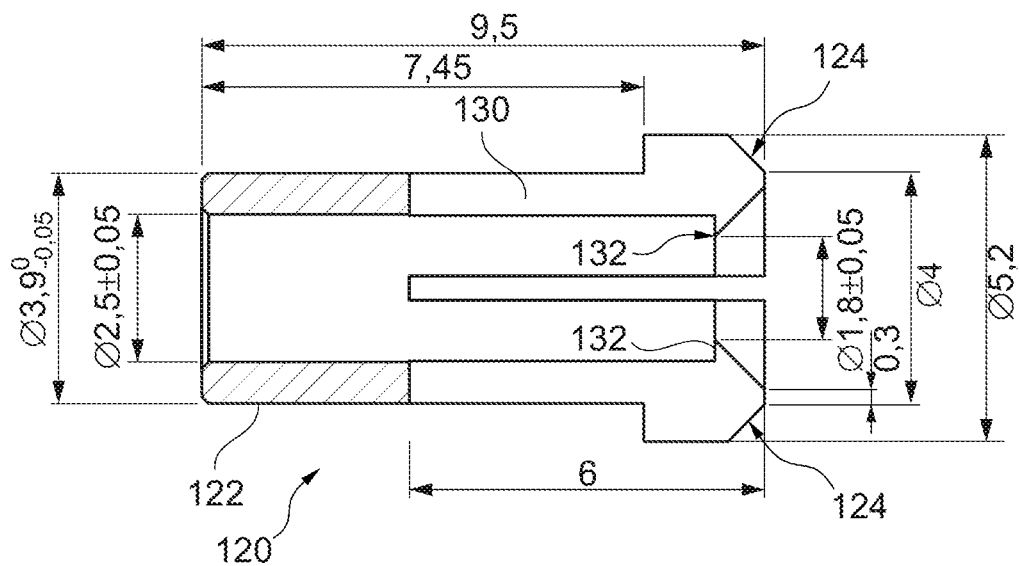
SECTION A-A  Fig. 8

MEDICAL DEVICE HOLDING AND DELIVERY ASSEMBLY AND KIT THEREFOR

RELATED APPLICATIONS

This application claims priority under 35 U.S.C. § 119 to Great Britain Patent Application No. 1904143.3, filed Mar. 26, 2019, entitled "MEDICAL DEVICE HOLDING AND DELIVERY ASSEMBLY AND KIT THEREFOR", the entire disclosure of which is hereby incorporated by reference.

BACKGROUND

1. Technical Field

The present invention relates to a medical device holding assembly, to a kit for deploying a medical device and to a method of providing an endoluminal medical device for a surgical procedure.

2. Background Information

The present invention lies in the field of storage and manipulation of implantable medical devices typically deployed endoluminally within the vasculature of a patient. It is common to deploy such devices through a percutaneous entry point, via a delivery catheter or sheath of an introducer assembly that may be pre-positioned into the patient, for example using the well known Seldinger technique. Once the delivery catheter or sheath is positioned as required within the vasculature of the patient, the clinician will deliver the medical device through the catheter from the percutaneous entry point. In some cases, particularly medical devices that are supplied in elongated form such as embolization coils or similar occluders, the device is housed in a holding sheath having at its distal end a connector, such as a Luer lock, able to be attached to the delivery catheter or sheath. Often, the holding sheath is fitted to a carrier for ease of transportation and storage, as well as for assuring the integrity of the medical device until it is deployed.

In the case particularly of elongate medical devices such as embolization coils, it is a common practice that the clinician will detach the holding sheath from the carrier before commencing the device deployment, for a variety of reasons including that existing carriers are not easily handled. However, this practice results in risk to the integrity of the medical device, particularly risk of squashing or kinking of the sheath and device. Furthermore, it often results in the need for two people to handle the holding sheath and medical device, which also further complicates the deployment operation.

Examples of mechanisms for fixing components of or in an introducer assembly include: US 2018/0242978, US 2007/0016166, U.S. Pat. Nos. 8,523,873, 9,981,118, US 2012/0041426 and U.S. Pat. No. 7,214,220.

BRIEF SUMMARY

The present invention seeks to provide an improved medical device holding assembly, a kit and an improved method of providing an endoluminal medical device for a surgical procedure, as well as improved deployment of medical devices. The invention is particularly, although not exclusively, suitable for the deployment of implantable medical devices provided in elongate form, such as embolization coils and other occluders.

According to an aspect of the present invention, there is provided a medical device holding assembly including: a sheath having a lumen therein within which an endoluminal medical device is in use held; a body member or housing comprising at least one holding element configured to hold the sheath, a fixation device attached to the body member and coupled to the sheath, the fixation device including a locking element having an unlocked configuration allowing the sheath to slide relative to the body member and a locked configuration fixing the sheath to the body member, a lock actuator configured to lock permanently the locking element into the locked configuration.

The structure of the assembly ensures that the medical device remains held in the body member until deployment, typically through an introducer catheter or sheath. In the preferred embodiments, the sheath is held in a compacted form. For example, it may be held within a tubular holding element that is wound on itself, for example in the form of a spiral, coil or helix. In a preferred embodiment the holding element does not extend beyond the outer confines of the body member. The practical effect of this is that the length of sheath that needs to be handled by the clinician is reduced.

The body member acts as a housing for the holding member, and may be in the form of a cartridge, which may be substantially planar. Conveniently the cartridge is sized to be held in a single hand of a user.

Preferably, the locking element comprises at least one tooth that embeds into the sheath when in the locked configuration, and which optimally has a bite orientation transverse to a longitudinal direction of the sheath. In a preferred embodiment, the locking element comprises a series of arcuate teeth disposed on flexible fingers, the teeth being disposed in an annular arrangement in the transverse orientation.

The lock actuator may be a compression element configured to force the tooth or teeth onto the sheath surface, the compression element being preferably fixable in a compression configuration. In a practical embodiment, the compression element is a locking nut, fixable or fixed in a locking configuration. The locking nut may be fixable or fixed by one or more of: torque tightening, one-way closure mechanism, bonding, gluing, welding, or any other suitable fixation system.

Advantageously, the lumen of the sheath has a substantially uniform diameter through the fixation device.

In a practical embodiment, the body member is a substantially planar cartridge. The sheath may be held in a spiral in the body member, that is, on the planar cartridge.

The fixation device may comprise at least one tube arranged in a spiral, the sheath being held in the tube.

Preferably, the fixation device includes a flush chamber in communication with the at least one tube. There may be provided a fluid seal between the locking element and the flush chamber.

Preferably the assembly includes a pusher element, for example, a pusher rod in the holding element. In a preferred embodiment the holding element is provided in two sections, with a gap between the two sections through which the pusher element is exposed. The pusher element is thus accessible to a user.

Advantageously, the sheath is fixed to the body member with a mandrel sized to the lumen of the sheath and disposed across the locking element when converted to the locking configuration.

In practice, a medical device is held within the sheath, the medical device being slidable from the sheath for deployment. The medical device may be an implantable medical device, for example an occlusion device such as an embolization coil.

According to another aspect of the present invention, there is provided a medical device introducer kit, including a medical device holding assembly according to any preceding claim and an introducer assembly comprising a deployment catheter endoluminally deployable in a patient, the deployment catheter including a distal end and a proximal end, the proximal end being connectable to the holding sheath for transfer of a medical device held in the holding sheath to the catheter for deployment into a patient.

Advantageously, the kit includes a connector on the catheter for attaching the catheter and the sheath together.

According to another aspect of the present invention, there is provided a method of providing an endoluminal medical device for a surgical procedure, the medical device being held in a medical device holding assembly including: a sheath having a lumen therein within which the endoluminal medical device is held; a body member comprising at least one holding element configured to hold the sheath, a fixation device attached to the body member and coupled to the sheath, the fixation device including a locking element; the method including the steps of: disposing the sheath in the body member by means of the at least one holding element, arranging a distal portion of the sheath to extend beyond the body member, setting the locking element into a permanent locked configuration thereby to fix the sheath to the body member; and disposing the medical device in the lumen of the sheath for storage and use.

The locking element may be set into a permanent locked configuration by means of a lock actuator, the lock actuator being fixable in a locking configuration.

The method preferably includes the step of locking the sheath to the body member by embedding at least one tooth of the locking element into the sheath. The sheath may be locked to the body member by one or more of: torque tightening, one-way closure mechanism, bonding, gluing, welding.

Advantageously, the sheath is held in a spiral in the body member.

The method preferably includes the step of fixing the sheath to the body member with a mandrel sized to the lumen of the sheath and across the locking element when the locking element is set to the locking configuration.

The method may include the step of attaching the sheath to a catheter of a medical introducer assembly.

Other aspects, features and advantages of the teachings herein will become apparent to the skilled person having regard to the description of preferred embodiments that follows.

BRIEF DESCRIPTION OF THE DRAWINGS

Embodiments of the present invention are described below, by way of example only, with reference to the accompanying drawings, in which:

FIGS. 2A to 2C are schematic diagrams of an example of embolization coil delivery apparatus for use in the kit disclosed herein;

FIGS. 4 to 6 are diagrams of a preferred embodiment of fixation device for the holding assembly of FIG. 3.

FIGS. 7 to 10 are diagrams of an embodiment of retention collet for the fixation device of FIGS. 4 to 6.

DETAILED DESCRIPTION OF THE DRAWINGS AND EMBODIMENTS

Figure 1:
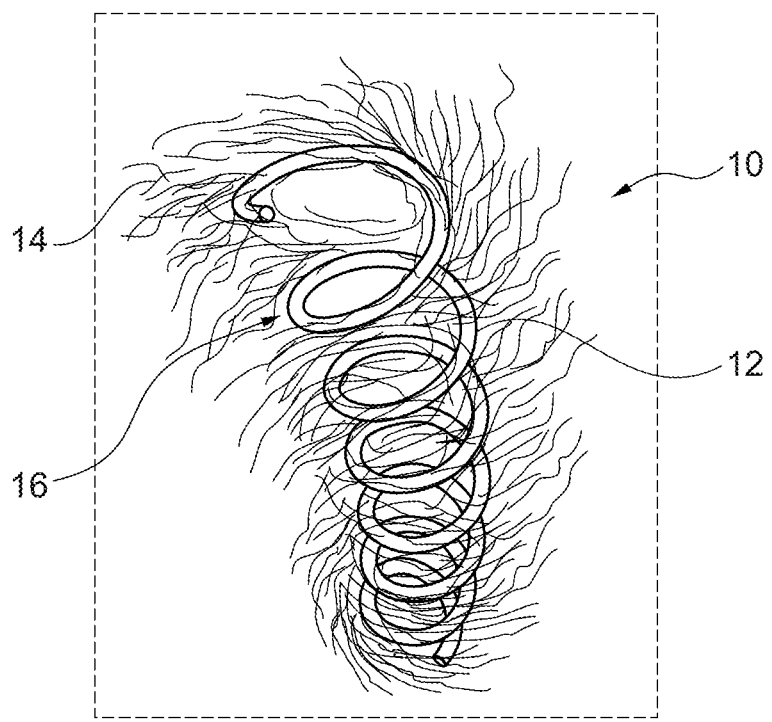
FIG. 1 is a schematic diagram of an example of embolization coil.
Figure 7:
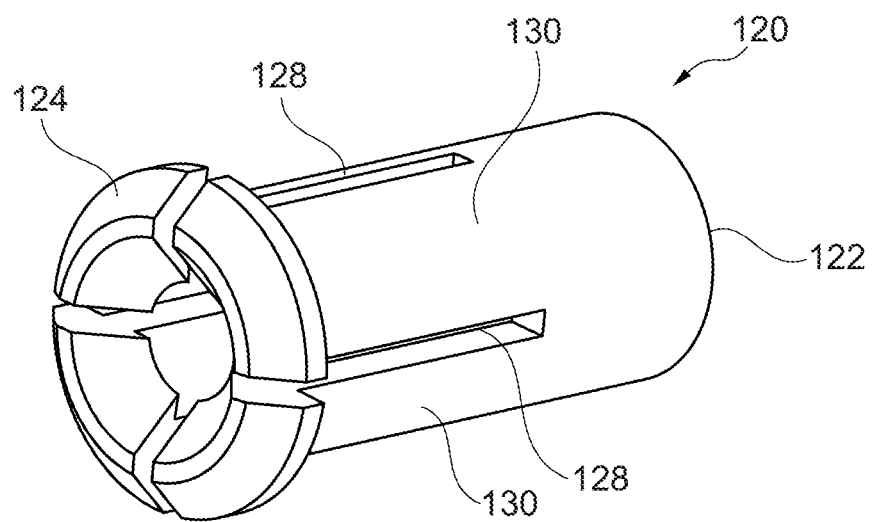

It is to be understood that the drawings are schematic only and not to scale. Furthermore, the drawings depict only the principal elements of the described structures.

Furthermore, while some dimensional indications are given in the drawings and description for some of the components, these are exemplary only and not intended to be limiting.

The embodiments disclosed below focus on the handling and deployment of occlusion devices, in particular embolization coils. However, it is to be understood that the teachings herein are not restricted to a specific type of medical device.

Referring to FIG. 1, an example of an embolization coil 10 is shown. This is representative of the applicant's Nester® Embolization Coil, being one of many embolization coils produced and sold by the applicant. The embolization coil 10 shown in FIG. 1 includes an elongate element 12 which may be formed as a coil of soft platinum wire, to which there are attached embolization fibres 14 for promoting embolization of blood around the coil. Such coils will tend to have a natural, unbiased, form in which the main coil 12 winds in helical form with turns 16 of generally uniform turn diameter, or in any other bundled shape so as in practice to fill the cavity of a vessel into which they are deployed. Such coils 10, however, are generally provided in a straight, linear, configuration within a delivery catheter of an introducer device and they will adopt their coiled or bundled form when released from the delivery catheter. Such coils 10 can have significant length, often being many tens of centimetres or more.

It will be appreciated that FIG. 1 shows only one example of a variety of medical devices suitable for the apparatus and method taught herein.

FIGS. 2A to 2C illustrate a body cavity embolization catheter assembly 20 for delivering an embolization device 10 such as that shown in FIG. 1 endoluminally into a patient's vessel. The assembly 20 includes an inner catheter 22 preferably made of a soft, flexible material such as silicone or any other suitable material. The inner catheter 22 has a proximal end 24, a distal end 26, and an adapter or hub 28 to receive apparatus to be advanced therethrough. In this embodiment, the inside diameter of the inner catheter 22 may range between 0.25 and 0.80 millimetres. The apparatus 20 also includes a guide wire 30 for guiding a guide catheter 32 during insertion of the guide catheter 32 into a body cavity. The guide catheter 32, which is preferably made of or coated with polytetrafluoroethylene (PTFE), assists in the percutaneous deployment of the inner catheter 22 in a body cavity. The guide catheter 32 may have a size of about 1.2 to 2.4 millimetres. The guide catheter 32 is typically provided with a hub 34 at its proximal end, the hub having a haemostatic valve closing its lumen for the prevention of loss of bodily fluids when used. The adaptor hub 28 attached to the inner catheter 22 will typically also be provided with a haemostatic valve. The dimensions given in this paragraph are exemplary only and not intended in any way to be limitative.

With the distal end 26 of the inner catheter 22 positioned in use at the point for occlusion in the body cavity, the occluding device 10 is loaded from the proximal end 24 of the inner catheter 22, through an opening at the proximal end of the hub 28 and is advanced through the internal lumen of the inner catheter 22 for deployment through the distal end 26. The occluding device 10 may be advanced over the guide wire 30, or the guide wire 30 may be removed and replaced by the occluding device 10. A push wire 40 may be used to advance or push the occluding device 10 through the inner catheter 22.

The embolization coil of the device 10 is extended into an approximately linear configuration, such that the secondary coil 16 of the device 10 is not present until the device 10 is deployed, that is withdrawn, from the inner catheter 22. In other words, the device 10 may have a substantially linear configuration in the collapsed state, as shown FIG. 2C. As the device 10 exits the distal end 26 of the inner catheter 22 it will begin to curl back to its unbiased shape, that is the secondary loops 16 will reform, to the extent they can within the confines of the lumen in which the coil 10 is deployed.

It is to be understood that the catheter apparatus 20 shown in FIGS. 2A to 2C is merely one example of apparatus that may be used to deploy a medical device into a body vessel.

The occlusion device 10 may be deployed within a body vessel by first loading it from a cartridge (described in further detail below) through the hub 28 at the proximal end 24 of the inner catheter 22 and the device 10 advanced, optionally by the pusher wire 40, towards the inner catheter distal end 26. The distal portion of the occlusion device 10, that is the first loop of the secondary coil 16, is positioned at the desired point of occlusion in the body vessel, while the remaining portion of the device 10 is held in the inner catheter 22. The first portion will hold the device 10 in place within the vessel. When the distal portion of the device 10 is at the desired point of occlusion in the body vessel, the remainder of the device 10 is pushed out from the inner catheter 22 and will fold or curl across the lumen of the body vessel to pack the device 10 into the vessel and occlude it. In some cases, the inner catheter 22 may be moved back and forth during its deployment, which will assist in folding the device 10 into a packed state in the vessel, thereby optimising occlusion.

Figure 3:
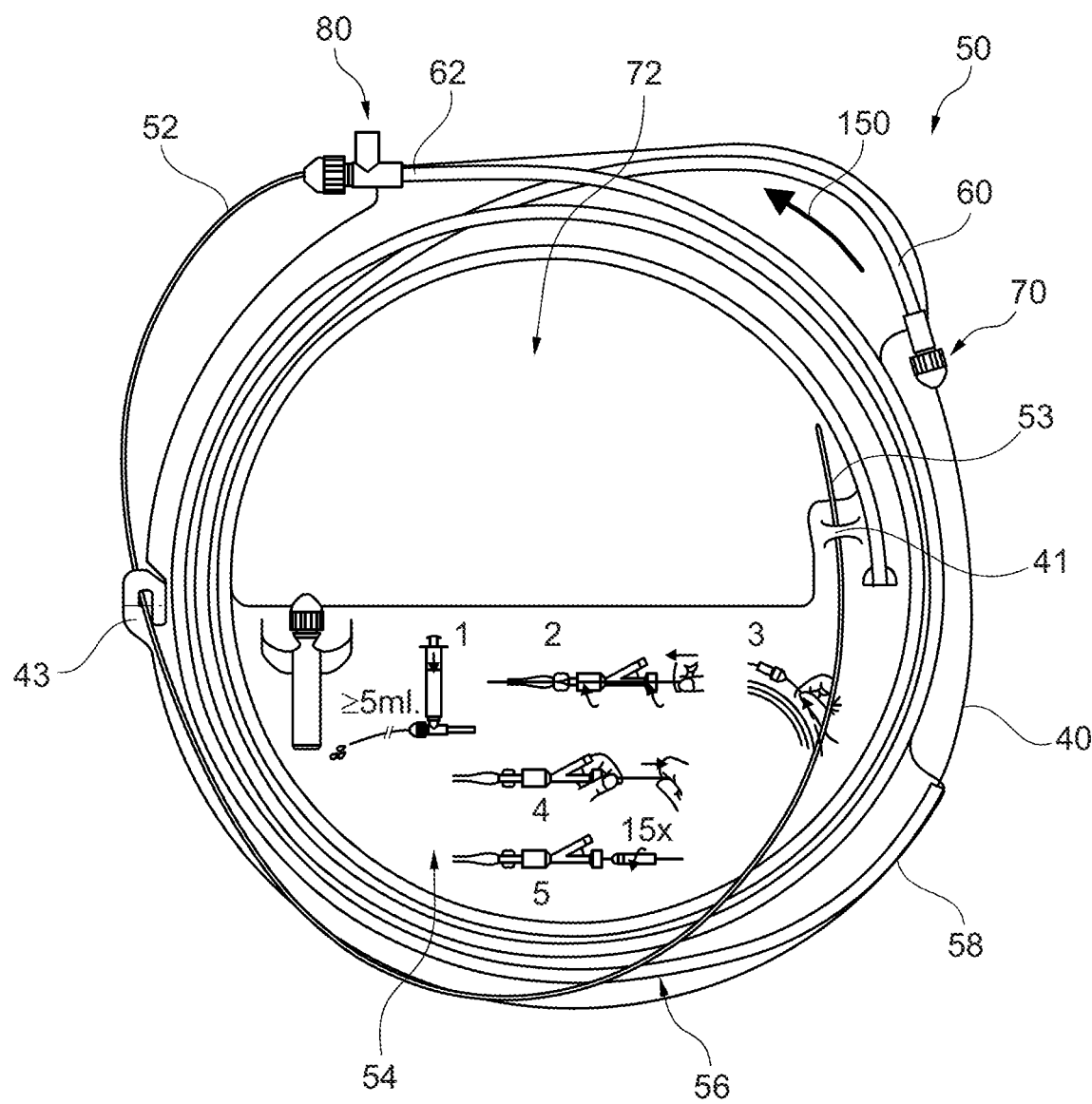
FIG. 3 is a schematic diagram of an embodiment of medical device holding assembly.

Referring now to FIG. 3, this shows an embodiment of medical device holding assembly 50 for use in holding a medical device, such as an embolization coil 10 of the type shown in FIG. 1, for transportation and that enables the feeding of the medical device 10 into a catheter of an introducer assembly, such as the inner catheter 22 of the assembly 20 shown in FIGS. 2A-2C. The apparatus 50 includes a sheath 52 having a lumen therein and of a length sufficient to hold at least the entirety of the medical device 10 when in its straightened configuration and also pusher element, such as a pusher rod or wire 40 used for pushing the medical device 10 through the sheath 52 and the inner catheter 22 of the delivery assembly 20.

The apparatus 50 also includes a body member or housing 54, which in this example is in the form of a flat cartridge made of any suitable material, typically a plastics or plasticised material. Attached to the housing 54 is a holding element in the form of a tube 56 within which the sheath 52 holding the medical device 10 can be placed. The tube 56 is relatively rigid compared to the sheath 52 and in this embodiment is arranged spirally around the perimeter of the body member 54 so as to hold the sheath in a compacted form. In this embodiment, this tube 56 is in two parts, a distal portion 60, and a proximal portion 58, which are separated from one another by a gap (in this embodiment for an arc of a circle). The sheath 52 containing the medical device 10 is located within the distal portion 60 of the tube 56. The pusher 40, located within the sheath 52 proximally of the medical device 10 extends beyond the proximal end of the sheath 52, across the gap between the distal and proximal portions 60, 58 of the tube 56, and into the proximal portion 58 of the tube 56. The pusher 40 is thus exposed, enabling a clinician to move the pusher 40 by hand through the distal tube portion 60 towards an exit 62 of the tubing 56.

There is provided in this embodiment a releasable locking device 70, typically a compression gripper of a type known in the art, for locking the pusher 40 in position and preventing it from being moved inadvertently through the distal tube portion 60, typically during transportation, storage and manipulation prior to clinical use. The locking device 70 may include any suitable compression element of a type known in the art.

In some embodiments the housing 54 may be a cartridge. It is preferably sized and shaped to be held in one hand of a user. It preferably includes at least one cut-out 72 sized such that a clinician can put his or her fingers through the cut-out to hold the assembly 50 and grip the cartridge with one hand, typically with the peripheral portion of the cartridge by the cut-out held in the palm of the hand.

Typically, the tubing 56 is permanently fixed to the body member 54 so that they form a unitary device.

At the exit 62 of the tubing 56 there is provided a fixation device 80, described in detail below. The fixation device 80 is fixedly attached at one end to the tubing 56 and includes a bore or lumen therethrough, through which the sheath 52 carrying the medical device 10 can pass. As described in detail below, the fixation device 80 includes a locking element which can be unlocked during assembly of the apparatus 50, to enable a distal portion of the sheath 52 to be located outside the tubing 56, and has a locked configuration which fixes the sheath 52 to the housing 54. The fixation device includes a lock actuator, also described in detail below, which is configured to lock permanently the locking element into a locked configuration. In other words, once assembled, the fixation device 80 fixes the sheath 52 to the housing 54 such that the sheath 52 cannot be removed by a clinician during the device deployment process. This contrasts with prior art systems, which allow for the sheath 52 to be removed from the holding assembly and which results in the sheath 52, with the medical device 10 and pusher 40 still held therewithin, to be handled during the device deployment process. This can be problematic because the sheath 52 and pusher 40 can be of substantial length, requiring the assistance of a second person in order to ensure integrity of the medical device 10 and pusher 40 and to prevent damage to this, such as by kinking of the sheath 52 and/or medical device.

The distal end 53 of the sheath 52 is conveniently held temporarily to the holder 54 by means of two clips 41, 43. The distal end 53 can be unclipped from the clips 41, 43 when ready to be fed into a hub (not shown) of a delivery catheter 22 and locked in place by a compression lock or similar device known in the art. Once coupled together, given the arrangement of the holding assembly 50 shown in FIG. 3, a clinician can manipulate the apparatus 50 and deploy the medical device 10 without assistance from a second person, as it is not necessary to support the sheath 52 separately. In other words, the clinician can use one hand to hold the housing 54 and a second hand to move the pusher 40 in order to feed the medical device 10 through the sheath 52 and into the delivery catheter 22.

The tip 53 of the sheath 52 is preferably tapered to assist in its insertion into the hub 28 of the delivery catheter assembly 20.

Usefully, the housing 54 could be provided with usage instructions, for instance of graphical form, as can be seen in FIG. 3.

Figure 4:
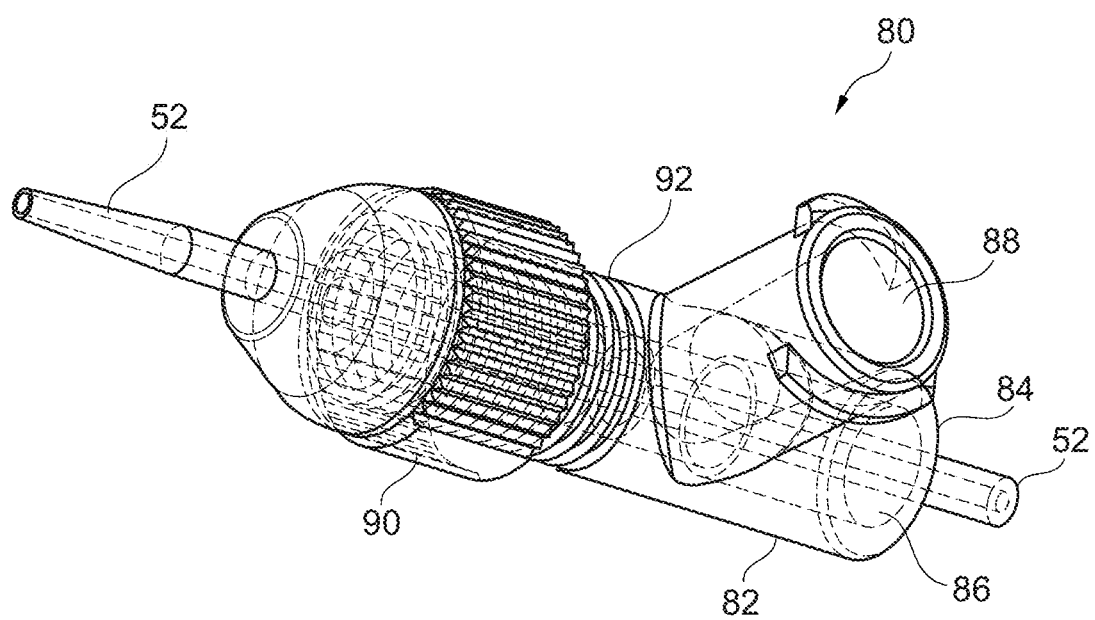
Figure 5:
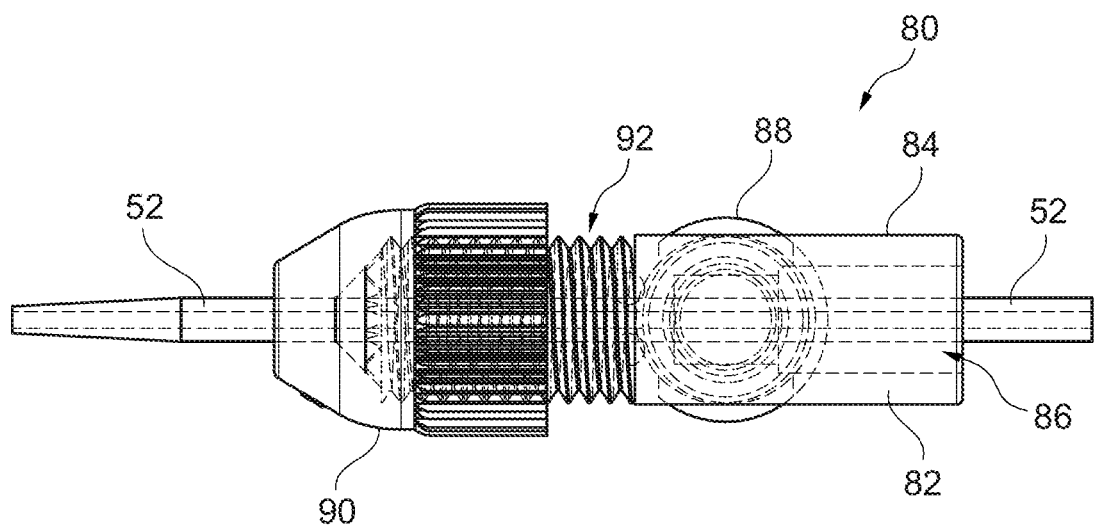
Figure 9:
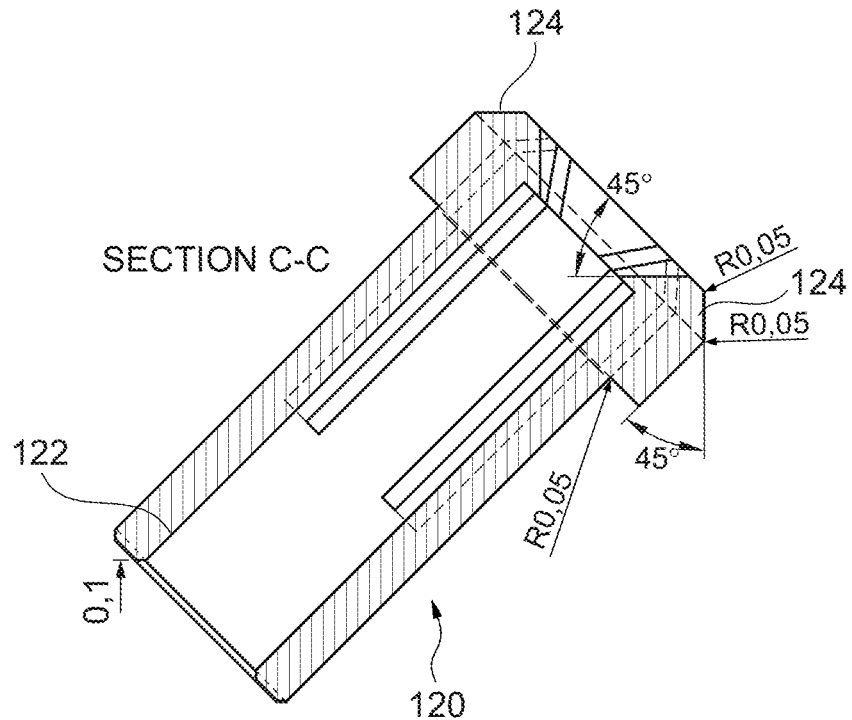
Figure 10:
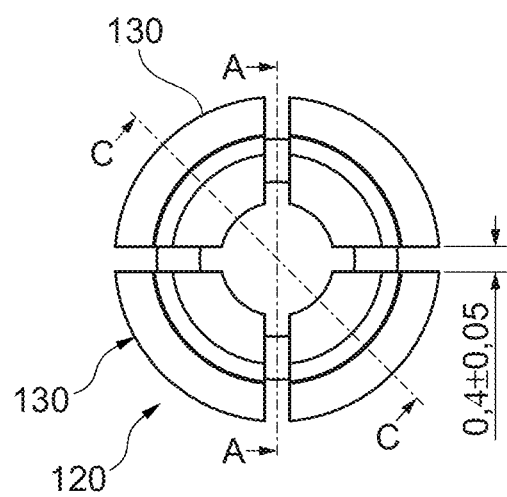

Referring now to FIGS. 4 to 6, these show a preferred embodiment of fixation device 80 of the assembly 50. The fixation device 80 includes a hub 82 having a chamber and lumen therein through which the device holding sheath 52 can pass. In FIGS. 4 to 6, only a short portion of the distal end of the sheath 52 is shown extending out of the fixation device 80 but it will be appreciated in practice that a much longer section, for example as shown in FIG. 3, would be positioned beyond the fixation device 80.

The hub 82 of the fixation device also includes at its proximal end 84 a portion 86 of enlarged inner diameter, sized to receive the end 62 of the tubing 56, to which in practice it is attached, for example, by gluing, bonding or by a friction fit. Thus, the fixation device 80 is fixed to the tubing 56. The fixation device 80 also includes a port 88 in fluid communication with the lumen of the hub 82, used for flushing the apparatus, typically with saline solution as conventional in the art. The port 88 may be provided with a Luer fitting for connection to a suitable supply of flushing fluid.

At the distal end of the hub 82 there is provided a lock actuator 90 which in this embodiment is a locking nut that fits onto and engages with a threaded portion 92 of the hub 82. The locking nut can be released in order to set the locking element 80 into an unlocked configuration, allowing sliding of the sheath 52 into and out of the hub 82 and can be locked so as to fix the sheath 52 relative to the hub 82 and to prevent any sliding of the sheath 52 relative to the hub 82. The locking nut 90 is able to be locked permanently into a locked configuration and this can be achieved in one of a plurality of ways, for example by torque tightening, by a one-way closure mechanism, by bonding, by gluing, by welding and so on.

Referring now specifically to FIG. 6, this shows a longitudinal cross-sectional view through the fixation device 80 of FIGS. 4 and 5. The internal chambers of the hub 82 of the fixation device 80 are effectively divided into two by means of a compression seal 100, typically an O-ring seal which in use is compressed against an inner annular wall 102 of the hub body 82. The seal 100 isolates a distal part 104 of the fixation device 80 from flushing fluid fed through the flushing port 88. On the other hand, the proximal section 106 of the hub 82 is in fluid communication with the flush port 88, which in practice will enable flushing fluid to pass proximally into end 62 of the distal portion 60 of the tubing 56 and in practice also into the sheath 52 so as to flush the inner lumen 55 of the sheath 52 with flushing fluid.

Located within the distal portion 104 of the hub 82 is a locking element 120 shown and described in further detail in FIGS. 7 to 10, to which reference is now made. The dimensions shown in the Figures are exemplary only and not intended in any way to be limitative.

The fixation element 120 includes a proximal end 122, which in practice abuts against the seal 100, and a distal end 124 that includes a chamfered annular outer surface 124 which co-operates with an inner chamfered surface 160 of the compression nut 90. The arrangement is such that when the nut 90 is tightened, towards the seal 100, the locking element 120 is pushed towards the seal 100, which compresses longitudinally and seals against the annular wall 102, and also presses the distal end of the locking device radially inwardly, that is towards the sheath 52. This can be seen in particular in FIGS. 7 and 10. The distal end of the locking element 120 is provided with a number of longitudinal slots 128 which form cantilevered fingers 130. At the end of each cantilevered finger 130 there is provided a tooth 132 extending radially inwardly and a part circular form and extending transverse to the longitudinal direction of the element 120 and, in practice, of the sheath 52. The teeth 132 are particularly visible in FIGS. 8 and 9.

As a result, when the locking nut 90 is turned to its locking configuration in order to press the locking element 120 against the seal 100 and the annular wall 120, the cantilevered fingers 130 are pressed radially inwards, causing the teeth 132 to dig into the outer surface of the sheath 52. This locks the sheath 52 to the fixation device 80 and as a result to the body member 54 given that the tubing 56 is also fixed to the body member 54. With the locking nut 90 fixed in its locked configuration, the sheath 52 becomes permanently fixed to the body member 54.

In a preferred embodiment, in order to maintain the integrity of the sheath 52 and in particular the uniformity of its inner lumen 55 during assembly, once the sheath 52 has been positioned as desired with respect to the tubing 56 and the fixation device 80, a mandrel 140, shown in dotted outline in FIG. 6, is inserted into the lumen 55 of the sheath 52 and the locking nut 90 then tightened to the locking position. The mandrel is preferably sized to be a close fit within the lumen 55 of the sheath 52. The mandrel 140 prevents the sheath 52 from collapsing radially inwardly and ensures that the uniformity of the lumen 55 is maintained, that is it internal lumen wall remains smooth and does not compressed inwardly. Once the sheath 52 is locked in position, the mandrel 140 can be removed and the medical device then inserted into the sheath 52.

It will be appreciated that in some practical implementations the holding assembly 50 depicted in FIG. 3, together with the associated implantable medical device, may be provided for attachment to a delivery catheter of an introducer assembly provided separately for the intended clinical use. In other practical implementations, the holding assembly 50 will be provided as a kit with an introducer assembly comprising a deployment catheter, with an appropriate operating connector to attach to the distal end 53 of the sheath 52, and other components associated with the introducer assembly, which are well known in the art and therefore not described in detail herein.

While the method of assembly of the device 50 of FIG. 3 and its use will be apparent to the person skilled in the art having regard to the disclosure above, for the sake of completeness, the device 50 is assembled by attaching the holding tubing 56 to the housing 54, preferably in a spiral formation as shown in FIG. 3. The attachment may be by mechanical fixings, bonding, welding, gluing or any other suitable mechanism. As described above, the tubing 56 is provided and disposed in two sections a proximal section 58 and a distal section 60 with a gap between the two sections being provided as shown, through which the pusher 40 can be manually accessed. The fixation device 80 is arranged in a non-locking configuration, as is the safety lock 70. The sheath 52 is then fed through the tubing 56 until a desired length of the sheath 52 extends beyond the cartridge 54 and the fixation device 80. With mandrel 140 inserted in the sheath 52 (which can be done, if desired, prior to feeding the sheath 52 into the tubing 56), the nut 90 of the fixation device 80 is tightened, causing the O-ring seal 100 to compress into a sealing configuration and the teeth 132 of the locking element 124 to dig into the outer surfaces of the sheath 52. The mandrel 140, as explained above, ensures that the internal lumen 55 of the sheath 52 is not compressed and remains of uniform diameter and smooth walled. The nut 90 is fixed in the closed position by any of the methods described above and the mandrel 140 is then removed. The medical device can then be fed into the sheath 52, by any of the known methods, and the pusher rod 40 typically temporarily attached to the medical device for implantation, is passed through the safety lock 70 and into the second, distal portion 60 of the tubing 56. Once the medical device is correctly positioned within the sheath 52, the safety lock 70 is tightened onto the pusher element 40, thereby fixing the medical device within the sheath.

For deployment, after sterilization, the distal end 53 of the sheath 52 is coupled to a coupling element 28 of an introducer catheter and tightened thereto in any convenient manner. This would typically be by a compression coupling of known form. Once connected together, the assembly is flushed with saline solution and the safety lock 70 released once the clinician is ready to commence the device deployment process.

The housing 54 can be held in one hand by the clinician, who can use the other hand to feed the pusher element 40 through the tubing 56 by moving it across the gap between the tube distal and proximal sections 60, 58. The housing 54 advantageously includes a marking such as an arrow 150 (shown in FIG. 3) indicating the direction in which the pusher 40 must be slid in order to push the medical device 10 out through the distal end 53 of the sheath 52.

Given that the fixation element 80 is permanently fixed in a locked condition, the carrier sheath 52 cannot be removed from the body member of the holding assembly, thereby assuring facilitation of the deployment process and the integrity of the medical device prior to its deployment in a patient.

It is to be appreciated that the above disclosure is of a preferred embodiment and that modifications may be made while still benefiting from the teachings herein. For example, while the locking element 120 is shown to have four fingers and four teeth, there may be provided a different number of teeth, even one tooth will do, and that these do not necessarily have to extend circumferentially. Similarly, the teeth do not need to have an arcuate shape or to be disposed in an annular arrangement, they could have any other suitable shape including as one or more pointed tips and could be disposed a different longitudinal relative to one another.

While in the preferred embodiment the sheath 52 has a uniform diameter along its length, in other embodiments it may have changing diameters, for instance in dependence upon the nature of the diameter or diameters of the medical device and pusher held therewithin.

The housing 54, typically the cartridge, is preferably planar but could have any other convenient shape, preferably allowing its holding with one hand.

The fluid seal 100 may be omitted in some embodiments, particularly in cases where the distal portion of the hub 80 is sealed.

In some embodiments, the distal end 53 of the sheath 52 may be provided with a coupling member that co-operates with a coupling member at the proximal end of the delivery catheter 22.

While the tubing 56 is preferably arranged in spiral form, in other embodiments it could be disposed in other arrangements, including helical, conical, and so on.

Throughout this specification various indications have been given as to preferred and alternative examples and aspects of the invention. However, the foregoing detailed description is to be regarded as illustrative rather than limiting and the invention is not limited to any one of the provided aspects. It should be understood that it is the appended claims, including all equivalents, that are intended to define the spirit and scope of this invention.

The invention claimed is:

1. A medical device holding assembly comprising:
a sheath having a lumen therein within which a medical device is held, the medical device being slidable from the sheath for deployment;
a housing comprising at least one sheath holding element having a generally cylindrical shape and a distal end, a fixation device attached to the housing via the distal end of the sheath holding element and coupled to the sheath, the fixation device including a compressible locking element disposed about the sheath having an unlocked configuration allowing the sheath to slide relative to the housing and a locked configuration fixing the sheath to the housing, and a rotatable lock actuator engaged with the locking element configured to lock permanently the compressible locking element into the locked configuration, thereby permanently fixing the sheath to the housing,
wherein the at least one sheath holding element holds the sheath in a compact form.

2. The assembly of claim 1, wherein the compressible locking element comprises at least one tooth that embeds into the sheath when in the locked configuration, optionally wherein the at least one tooth has a bite orientation transverse to a longitudinal direction of the sheath, further optionally wherein the compressible locking element comprises a series of arcuate teeth disposed on flexible fingers, the teeth being disposed in an annular arrangement in the transverse orientation.

3. The assembly of claim 2, wherein the rotatable lock actuator is a compression element configured to force the tooth or teeth to the sheath.

4. The assembly of claim 3, wherein the compression element is fixable in a compression configuration.

5. The assembly of claim 3, wherein the compression element is a locking nut, fixable in a locking configuration.

6. The assembly of claim 5, wherein the locking nut is fixable by one or more of: torque tightening, one-way closure mechanism, bonding, gluing, welding.

7. The assembly of claim 1, wherein the lumen of the sheath has a substantially uniform diameter through the fixation device and/or wherein the housing is a substantially planar cartridge.

8. The assembly of claim 1, wherein the sheath is held in a spiral in the housing and/or wherein the at least one sheath holding element comprises at least one tube arranged in a spiral, the sheath being held in the tube.

9. The assembly of claim 1, wherein the fixation device includes a flush chamber in communication with the at least one sheath holding element, optionally including a fluid seal between the compressible locking element and the flush chamber.

10. The assembly claim 1, including a pusher element in the at least one sheath holding element, optionally wherein the at least one sheath holding element is provided in two sections, with a gap between the two sections through which the pusher element is exposed.

11. The assembly of claim 1, wherein the sheath is fixed to the housing with a mandrel sized to the lumen of the sheath and disposed across the fixation device when the compressible locking element is converted to the locked configuration.

12. The assembly of claim 1, wherein the medical device is an implantable medical device.

13. The assembly of claim 12, wherein the medical device is an occlusion device.

14. The assembly of claim 12, wherein the medical device is an embolization coil.

15. A medical device introducer kit, comprising
a medical device holding assembly comprising
a sheath having a lumen therein within which a medical device is held, the medical device being slidable from the sheath for deployment; and
a housing comprising at least one sheath holding element having a generally cylindrical shape and a distal end, a fixation device attached to the housing via the distal end of the sheath holding element and coupled to the sheath, the fixation device including a compressible locking element disposed about the sheath having an unlocked configuration allowing the sheath to slide relative to the housing and a locked configuration fixing the sheath to the housing, and a rotatable lock actuator engaged with the locking element configured to lock permanently the compressible locking element into the locked configuration, thereby permanently fixing the sheath to the housing; and,
an introducer assembly comprising a deployment catheter endoluminally deployable in a patient, the deployment catheter including a distal end and a proximal end, the proximal end being connectable to the sheath for transfer of the medical device held in the sheath to the catheter for deployment into the patient, optionally including a connector on the catheter for attaching the catheter and the sheath together,
wherein the at least one sheath holding element holds the sheath in a compact form.

16. A method of providing an endoluminal medical device for a surgical procedure, the endoluminal medical device being held in a medical device holding assembly comprising a sheath having a lumen therein within which the endoluminal medical device is held; a housing comprising at least one sheath holding element having a generally cylindrical shape and a distal end, a fixation device attached to the housing via the distal end of the sheath holding element and coupled to the sheath, the fixation device including a compressible locking element; the method comprising:
disposing the sheath in the housing by means of the at least one sheath holding element;
arranging a distal portion of the sheath to extend beyond the housing;
setting the compressible locking element into a permanent locked configuration thereby to fix the sheath to the housing; and
disposing the endoluminal medical device in the lumen of the sheath for storage before use,
wherein the endoluminal medical device is slidable from the sheath for deployment, and
wherein the at least one sheath holding element holds the sheath in a compact form.

17. The method according to claim 16, further comprising locking the sheath to the housing by embedding at least one tooth of the compressible locking element into the sheath.

18. The method of claim 16, wherein the compressible locking element is set into a permanent locked configuration by means of a rotatable lock actuator, the rotatable lock actuator being disposed about the locking element and fixable in a locking configuration.

19. The method of claim 16, further comprising disposing a mandrel sized to the lumen of the sheath within the lumen of the sheath and across the compressible locking element, and setting the compressible locking element to the locking configuration with the mandrel in place.

* * * * *